United States Patent
Yevich et al.

(10) Patent No.: US 6,821,976 B2
(45) Date of Patent: Nov. 23, 2004

(54) S-6-HYDROXY-BUSPIRONE

(75) Inventors: Joseph P. Yevich, Southington, CT (US); Robert F. Mayol, Burns, TN (US); Jianqing Li, Guilford, CT (US); Frank Yocca, Killingworth, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 176 days.

(21) Appl. No.: 10/201,063

(22) Filed: Jul. 22, 2002

(65) Prior Publication Data

US 2003/0022899 A1 Jan. 30, 2003

Related U.S. Application Data

(60) Provisional application No. 60/307,428, filed on Jul. 24, 2001.

(51) Int. Cl.[7] .................... A61K 31/506; C07D 401/14
(52) U.S. Cl. ................... 514/252.15; 544/230
(58) Field of Search ..................... 514/252.15; 544/230

(56) References Cited

U.S. PATENT DOCUMENTS 6,150,365 A * 11/2000 Mayol .................. 514/252.15
6,593,331 B2 * 7/2003 Camborde et al. ..... 514/252.18

OTHER PUBLICATIONS

Robichaud et al. in Annual Reports in Medicinal Chemistry, Vol. 35 pp. 11–20 (2000).*

Mayol, et al., "Pharmacokinetics and Disposition of 14C–Buspirone HCl After Intravenous and Oral Dosing in Man," Clin. Pharmacol. Ther., 37, p. 210, 1985.

Winslow, et al., "Serotonergic modulation of the rat pup ultrasonic isolation call: studies with 5HT1 and 5HT2 sub-type–selective agonists and antagonists," Psychopharmacology, 105, pp. 513–520, 1991.

* cited by examiner

*Primary Examiner*—Richard L. Raymond
*Assistant Examiner*—Hong Liu
(74) *Attorney, Agent, or Firm*—Richard P. Ryan

(57) ABSTRACT

The S-stereoisomer of 6-hydroxy-buspirone is an effective treatment for anxiety, depression, and other psychogenic disorders. The S-isomer may provide reduced potential for adverse effects and a longer duration of action compared to the racemic mixture and with buspirone.

7 Claims, No Drawings

S-6-HYDROXY-BUSPIRONE

CROSS REFERENCE TO RELATED APPLICATION

This non-provisional application claims priority from provisional application U.S. S No. 60/307,428 filed Jul. 24, 2001.

BACKGROUND OF THE INVENTION

The present invention relates to methods of treating anxiety and depression using S-6-hydroxy-buspirone and pharmaceutical compositions containing S-6-hydroxy-buspirone.

Buspirone, chemically: 8-[4-[4-(2-pyrimidinyl)1-piperazinyl]butyl-8-azaspiro(4,5)-decane-7,9-dione, is approved for the treatment of anxiety disorders and depression by the U.S. Food and Drug Administration. It is available under the trade name BUSPAR® from Bristol-Myers Squibb Company.

Studies have shown that buspirone is extensively metabolized in the body. (See, for example, Mayol, et al., *Clin. Pharmacol. Ther.*, 37, p. 210, 1985). One of the metabolites is 6-hydroxy-8-[4-[4-(2-pyrimidinyl)1-piperazinyl]butyl-8-azaspiro(4,5)-decane-7,9-dione having Formula I. This metabolite is also known as BMS 28674, BMS 442608, or

I

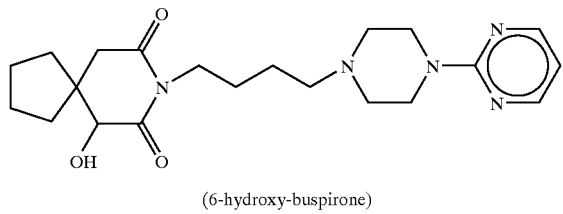

(6-hydroxy-buspirone)

as 6-hydroxy-buspirone. This compound is believed to be the active metabolite of buspirone and its use in treating anxiety disorders and depression is disclosed in U.S. Pat. No. 6,150,365. The specific stereochemistry of 6-hydroxy-buspirone has not been described previously. Neither racemic 6-hydroxy-buspirone nor its enantiomers are commercially available at the present time.

Preclinical studies demonstrate that 6-hydroxy-buspirone, like buspirone, demonstrates a strong affinity for the human 5-HT1A receptor. In functional testing, 6-hydroxy-buspirone produced a dose-dependent anxiolytic response in the rat pup ultrasonic vocalization test, a sensitive method for assessment of anxiolytic and anxiogenic effects (Winslow and Insel, 1991, *Psychopharmacology*, 105:513–520).

Clinical studies in volunteers orally dosed with buspirone demonstrate that 6-hydroxy-buspirone blood plasma levels were not only 30 to 40 times higher but were sustained compared to buspirone blood plasma levels. The time course of 6-hydroxy-buspirone blood plasma levels, unlike buspirone blood plasma levels, correlate more closely with the sustained anxiolytic effect seen following once or twice a day oral dosing with buspirone.

Although buspirone is an effective treatment for anxiety disorders and depression symptomatology in a significant number of patients treated, about a third of patients get little to no relief from their anxiety and responders often require a week or more of buspirone treatment before experiencing relief from their anxiety symptomatology. Further, certain adverse effects are reported across the patient population. The most commonly observed adverse effects associated with the use of buspirone include dizziness, nausea, headache, nervousness, lightheadedness, and excitement. Also, since buspirone can bind to central dopamine receptors, concern has been raised about its potential to cause unwanted changes in dopamine-mediated neurological functions and a syndrome of restlessness, appearing shortly after initiation of oral buspirone treatment, has been reported in small numbers of patients. While buspirone lacks the prominent sedative effects seen in more typical anxiolytics such as the benzodiazepines, patients are nonetheless advised against operating potentially dangerous machinery until they experience how they are affected by buspirone.

It can be seen that it is desirable to find a medicament with buspirone's advantages but which demonstrates more robust and/or long-lasting anxiolytic potency with a lack of the above described adverse effects.

Formation of 6-hydroxy-buspirone occurs in the liver by action of enzymes of the P450 system, specifically CYP3A4. Many substances such as grapefruit juice and certain other drugs; e.g. erythromycin, ketoconazole, cimetidine, etc., are inhibitors of the CYP3A4 isozyme and may interfere with the formation of this active metabolite from buspirone. For this reason it would be desirable to find a compound with the advantages of buspirone but without the drug-drug interactions when coadministered with agents affecting the activity level of the CYP3A4 isozyme.

SUMMARY OF THE INVENTION

It has now been discovered that the S-isomer of 6-hydroxy-buspirone is an effective treatment for anxiety disorders and depression which should not give rise to the adverse effects associated with buspirone, as well as having some advantage over racemic 6-hydroxy-buspirone. Therefore, in one aspect, the present invention relates to a method of treating anxiety disorders and depression, comprising administration to a person in need of such therapy a therapeutically effective amount of S-6-hydroxy-buspirone or a pharmaceutically acceptable salt thereof.

It has also been discovered that the S-isomer of 6-hydroxy-buspirone is useful in treating a number of other clinical disorders. Specifically, the present invention relates to methods of treating the following: extrapyramidal motor disorders; panic disorders such as panic attacks; agoraphobia, and phobic anxiety; short-term memory deficit; alcohol abuse and alcoholism symptomatology; nicotine dependence; drug addiction; eating disorders; post traumatic stress disorder; sleep-related respiratory disorders such as sleep apnea and sudden infant death syndrome; childhood autism; pre-menstrual syndrome; sexual dysfunction; agitation; hostility; obsessive-compulsive disorder; nausea and vomiting; incontinence; and acute and chronic pain.

Yet another aspect of the present invention goes to pharmaceutical compositions comprising S-6-hydroxy-buspirone and their administration for treatment of clinical disorders.

And in a further aspect, the invention relates to S-6-hydroxy-buspirone itself, substantially free of the R-enantiomer, or a pharmaceutically acceptable salt thereof.

DETAILED DESCRIPTION OF THE INVENTION

The active compound of the methods and compositions of the present invention is S-6-hydroxy-buspirone. The compound contains a chiral center that gives rise to the respective R- and S-spatial configurations. Neither enantiomer has been described in the literature. The structure of S-6-hydroxy-buspirone is shown in Formula II.

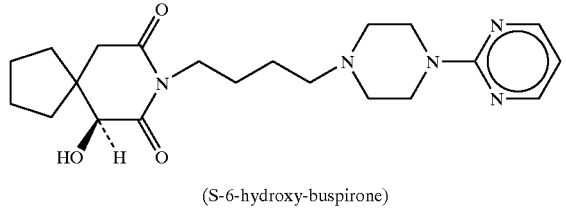

(S-6-hydroxy-buspirone)

The S-6-hydroxy-buspirone utilized for the methods and compositions of the present invention is substantially free of the R-stereoisomer of 6-hydroxy-buspirone, R-6-hydroxy-buspirone. The term "substantially free of the R-stereoisomer" as used herein means that the compound and compositions of the present invention contain a significantly greater proportion of the S-isomer of 6-hydroxy-buspirone in relation to the R-isomer of 6-hydroxy-buspirone. In a preferred embodiment of the present invention, the compositions contain at least 90% by weight of S-6-hydroxy-buspirone and 10% by weight or less of R-6-hydroxy-buspirone. More preferably, the compositions contain at least 98% by weight of S-6-hydroxy-buspirone and 2% by weight or less of R-6-hydroxy-buspirone, and in this case, the term "substantially free of the R-isomer" means that the compositions contain at least 98% by weight of S-6-hydroxy-buspirone and 2% by weight or less of R-6-hydroxy-buspirone. These percentages are based upon the total amount of 6-hydroxy-buspirone in the composition. The terms "substantially optically pure R-isomer of 6-hydroxy-buspirone" or "substantially optically pure S-6-hydroxy-buspirone" and "optically pure R-isomer of 6-hydroxy-buspirone" and "optically pure S-6-hydroxy-buspirone" are also encompassed by the above-described amounts.

The present invention also encompasses a pharmaceutical composition which comprises a pharmaceutically acceptable carrier and a therapeutically effective amount of S-6-hydroxy-buspirone or a pharmaceutically acceptable acid addition salt and/or hydrate thereof. Pharmaceutically acceptable acid addition salts of S-6-hydroxy-buspirone are those in which the anion does not contribute significantly to toxicity or pharmacologic activity of the base form of S-6-hydroxy-buspirone.

Acid addition salts are obtained either by reaction of S-6-hydroxy-buspirone with an organic or inorganic acid, preferably by contact in solution, or by any of the standard methods detailed in the literature and available to any practitioner skilled in the art. Examples of useful organic acids are carboxylic acids such as maleic acid, acetic acid, tartaric acid, propionic acid, fumaric acid, isethionic acid, succinic acid, pamoic acid, and the like; useful inorganic acids are hydrohalide acids such as HCl, HBr, Hl; sulfuric acid; phosphoric acid; and the like.

Any suitable route of administration may be employed for providing the patient with an effective dosage of S-6-hydroxy-buspirone. For example, oral, rectal, parenteral (including subcutaneous, intramuscular, and intravenous) routes may be employed. Sublingual, buccal, transdermal and transnasal routes of administration are also contemplated. Dosage forms include tablets, troches, dispersions, nasal sprays, suspensions, solutions, capsules and patches.

Compositions suitable for oral, buccal, sublingual, transdermal, transnasal, and parenteral administration are encompassed by the present invention. A preferred route of administration is oral. The compositions may be conveniently presented in unit dosage form and prepared by any of the methods well known in the art of pharmacy. Preferred unit dosage formulations are those containing an effective dose, or an appropriate fraction thereof, of the active ingredient, S-6-hydroxy-buspirone, or a pharmaceutically acceptable salt thereof.

S-6-hydroxy-buspirone may be prepared utilizing methods of synthesis and enantiomeric separation known to one skilled in the art. One method of preparation (Scheme 1) utilizes buspirone as a starting material to produce racemic 6-hydroxy-buspirone that is separated into the two enantiomers by chiral chromatographic techniques.

Scheme 1

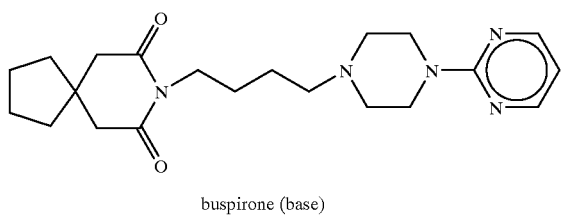

buspirone (base)

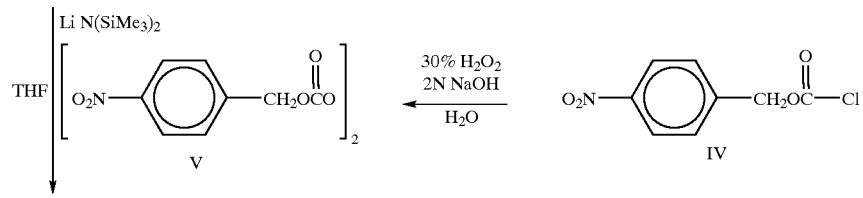

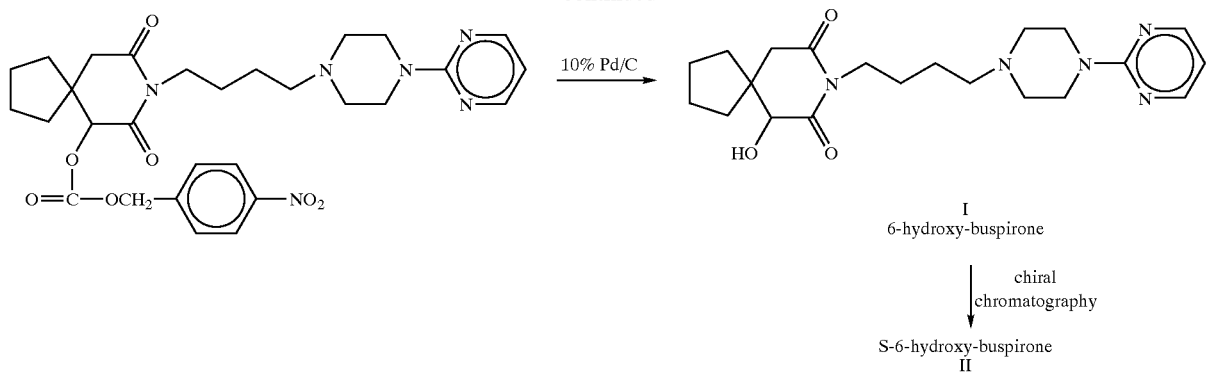

An improved one-step synthesis of racemic 6-hydroxy-buspirone is set forth in Scheme 2. Again, enantiomeric separation provides S-6-hydroxy-buspirone.

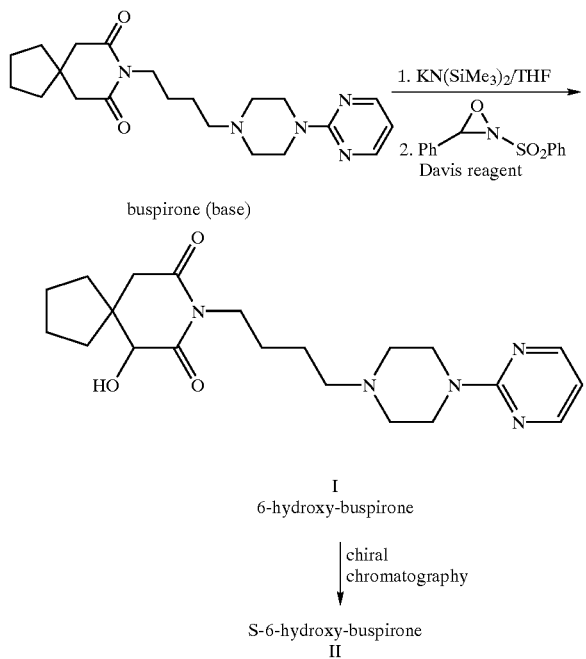

The present invention encompasses S-6-hydroxy-buspirone, substantially free of R-6-hydroxy-buspirone. The R- and S-isomers of hydroxy-buspirone may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomer may be synthesized by asymmetric synthesis using optically active reagents, substrates, catalysts or solvents, or by converting an enantiomer to the other by asymmetric transformation.

S-6-hydroxy-buspirone is believed to offer improved therapeutic treatment to sufferers of a variety of clinical disorders. Preclinical testing utilized ultrasonic vocalizations emitted by rat pups following isolation from their mother and littermates and subjected to a variety of environmental stimula (e.g., cold temperature). Statistically significant anxiolytic activity was demonstrated for both racemic 6-hydroxy-buspirone and S-6-hydroxy-buspirone at dose levels of 0.3 and 1 mg/kg s.c. However, animal movement, measured by crossing grid boundary lines, appeared to be reduced for the animals dosed with racemic 6-hydroxy-buspirone compared to the animals dosed with the single enantiomer. This difference between drug groups and animal movement suggests that S-hydroxy-buspirone may possess less side-effect potential than the racemate. These observations support a conclusion that adverse effects from racemic 6-hydroxy-buspirone such as sedation, dizziness, malaise, etc. that may act to inhibit animal locomotion, could be lessened in S-6-hydroxy-buspirone.

More importantly, pharmacokinetic studies with 6-hydroxy-buspirone have demonstrated the S-enantiomer is cleared more slowly from the bloodstream than the R-enantiomer. This reduced clearance (about three-fold) of S- over R- would favor the S-enantiomer in providing a more long-lasting duration of activity than the R- or the racemate.

Therefore, administration of S-6-hydroxy-buspirone could result in fewer adverse effects and a longer duration of action compared with the administration of the racemic mixture. One or more of the following adverse effects of the racemate may be reduced or avoided by administration of the S-enantiomer of 6-hydroxy-buspirone: dizziness, nausea, headache, nervousness, lightheadedness, excitement, and sedation.

Administration of S-6-hydroxy-buspirone pharmaceutical formulations to patients for the treatment of various clinical disorders is a major aspect of the present invention. The clinical disorders to be treated by administration of S-6-hydroxy-buspirone comprise the following: anxiety disorders; depression; anxiety mixed with depression; panic disorders such as panic attacks, agoraphobia, and phobic anxiety; extrapyramidal motor disorders; short-term memory deficit; alcohol abuse and alcoholism symptomatology; nicotine dependence; drug addiction; eating disorders; post traumatic stress disorder; sleep-related respiratory disorders such as sleep apnea and sudden infant death syndrome; pre-menstrual syndrome; childhood autism; agitation; hostility; obsessive-compulsive disorder; sexual dysfunction; incontinence; nausea and vomiting; and acute and chronic pain.

The magnitude of prophylactic or therapeutic dose of S-6-hydroxy-buspirone will vary with the nature and severity of the condition to be treated and the route of administration. The dose, and perhaps the dose frequency, will also vary according to the age, body weight and response of the individual patient. In general, the total daily dose ranges from about 5 mg per day to about 100 mg per day, preferably about 30 mg per day to about 60 mg per day, in single or divided doses. It is further recommended that children, patients over 65 years old, and those with impaired renal or hepatic function, initially receive low doses and that the dosage may be increased by titration based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with the individual patient's response.

The compositions of the present invention may also include a pharmaceutically acceptable carrier. The carrier may take a wide variety of forms, depending on the route of administration desired; for example, oral and parenteral (including intravenous). In preparing the composition for an oral dosage form, any of the usual pharmaceutical media may be employed, such as water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by a standard aqueous or nonaqueous techniques. Oral and parenteral sustained release dosage forms may also be used.

Oral syrups, a well as other oral liquid formulations, are well known to those skilled in the art, and general methods for preparing them are found in any standard pharmacy school textbook, for example *Remington: The Science and Practice of Pharmacy*. Chapter 86 of the 19$_{th}$ edition of Remington entitled "Solutions, Emulsions, Suspensions and Extracts" describes in complete detail the preparation of syrups (pages 1503–1505) and other oral liquids. Similarly, sustained release formulation is well known in the art, and Chapter 94 of the same reference, entitled "Sustained-Release Drug Delivery Systems," describes the more common types of oral and parenteral sustained-release dosage forms (pages 1660–1675). The relevant disclosure, Chapters 84 and 96, is incorporated herein by reference. Because they reduce peak plasma concentrations, as compared to conventional oral dosage forms, controlled-release dosage forms are particularly useful for providing a therapeutic plasma concentration of S-hydroxy-buspirone while avoiding the side effects associated with high peak plasma concentrations that occur with conventional dosage forms.

DESCRIPTION OF SPECIFIC EMBODIMENTS

The compound whose use constitutes this invention and its method of preparation will appear more fully in light of the following examples which are given for the purpose of illustration only and are not to be construed as limiting the invention in sphere or scope.

EXAMPLE 1

Preparation of 6-hydroxy-buspirone

A. Di-4-nitrobenzyl Peroxydicarbonate (V)

Di-4-nitrobenzyl peroxydicarbonate was prepared using a modification of the literature procedure[1]. Thus, to an ice-cold solution of 4-nitrobenzyl chloroformate (10.11 g, 4.7 mmol) in acetone (20 mL) was added dropwide over 30 min an ice-cold mixture of 30% $H_2O_2$ (2.7 mL, 24 mmol) and 2.35 N NaOH (20 mL, 47 mmol). The mixture was vigorously stirred for 15 min and then it was filtered and the filter-cake was washed with water and then with hexane. The resulting damp solid was taken up in dichloromethane, the solution was dried ($Na_2SO_4$) and then it was diluted with an equal volume of hexane. Concentration of this solution at 20° C. on a rotary evaptor gave a crystalline precipitate which was filtered, washed with hexane and dried in vacuo to give compound III (6.82 g, 74%) as pale yellow microcrystals, mp 104° C. (dec).

Di-4-nitrobenzyl peroxydicarbonate was found to be a relatively stable material which decomposed as its melting point with slow gas evolution. In comparison, dibenzyl peroxydicarbonate[2] decomposed with a sudden vigorous expulsion of material from the melting point capillary.

B. 6-(4-Nitrobenzyl Peroxydicarbonatyl)-8-[4-[4-(2-pyrimidinyl)-piperazinyl]-butyl]-8-aza To a solution of 8-[4-[4-(2-pyrimidinyl)-piperazinyl]-butyl]-8-azaspiro[4.5]-7,9-dione (buspirone: 10 g, 26 mmole) in dry THF (250 mL) was added LiN (Me$_3$Si)$_2$ (28.5 mL of a 1 M THF solution) at 78° C. and stirred for 3 h and then a solution of di-4-nitrobenzyl peroxydicarbonate (11.2 g) in dry THF (150 mL) was added dropwide over 1 h. Stirring was continued at −78° C. for 1 h.

The cooling bath was removed and the reaction solution was poured into a mixture of $H_2O$ and EtOAc. The organic phase was separated and washed with $H_2O$ and then brine. The organic base was dried and then evaporated to a viscous oil. Flash chromatography of this oil, eluting the silica column with MeCN-EtOAc (1:2) gave crude product which was washed with acetone, to remove unreacted buspirone, leaving 6.23 g of a white solid (46%) product (III).

C. 6-Hydroxy-8-[4-[4-(2-pyrimidinyl)-piperazinyl]-butyl]-8-azaspiro[4.5]-7,9-di

A mixture of III (4.0 g; 6.9 mmole) and 10% Pd/C (about 1 g) in MeOH (100 mL) was hydrogenated in a Parr shaker at 40–45 psi for 1 h. The hydrogenation mixture was filtered through a Celite pad which was then washed with EtOAc. The filtrate was evaporated to a gum which was purified by flash chromatography through a silica gel column eluting with EtOAc to give 0.41 g of an off-white solid (I).

Anal. Calcd. for $C_{21}H_{31}N_5O_3$: C, 62.82; H, 7.78; N, 17.44. Found: C, 62.84; H, 7.81; N, 17.33.

EXAMPLE 2

Enantiomeric Separation

Preparative Chiral HPLC Purification Procedure for 6-hydroxy-buspirone 1.1 g 6-Hydroxy-buspirone is dissolved in 55 mL HPLC grade methanol (20 mg/mL). Repetitive 0.5mL injections of the solution are made on a Chirobiotic-Vancomycin Chiral HPLC column, 22.1 mm×250 mm, 10 um particle size (Advanced Separation Technologies, Inc., Whippany, N.J.) equilibrated with a mobile phase of MeOH/acetic acid/triethylamine, 100/0.2/0.1, v/v/v, at a flow rate of 20 mL/minute. The UV trace is monitored at 236 nm. Each enantiomer (RTs ~10.9 and ~13.4 minutes, respectively) is collected in ~1000 mL of mobile phase and condensed separately under reduced pressure at 40° C. ~2 mL of clear solution resulting from the evaporation of methanol is diluted with 5 mL of $H_2O$. The pH of these solutions is adjusted from 5 to ~8 with $NH_4OH$, upon which a white precipitate is observed. The precipitates are centrifuged, and the aqueous layers extracted three times with equal volumes of methylene chloride. The methylene chloride layers are evaporated and any remaining solid is re-chromatographed. The centrifuged precipitates are washed three times with $H_2O$ to remove any residual salts and air dried at room temperature.

The basic form of S-6-hydroxy-buspirone can be converted to the hydrochloride salt by treatment of an ethanol solution of S-6-hydroxy-buspirone with ethanolic HCl.

EXAMPLE 3

One-Step Synthesis of 6-Hydroxy-buspirone (I)

Buspirone (19.3 g, 50 mmole) was dissolved in dry THF (400 mL) and the resulting solution was cooled to −78° C. A solution of $KN(SiMe_3)_2$ in toluene (100 mL, 1 M) was added slowly. After the reaction mixture was stirred at −78° C. for 1 h, a solution of 2-(phenylsulfonyl)-3-phenyloxaziridine (Davis reagent, prepared according to literature method: F. A. Davis, et al., *Org. Synth.*, 1988, 66, 203) (17.0 g, 65 mmole) in dry THF (150 mL, precooled to −78° C.) was added quickly via a cannular. After stirred for 30 mins at −78° C., the reaction was quenched with 1 N HCl solution (500 mL). It was extracted with EtOAc (3×500 mL). The aqueous layer was separated, neutralized with saturated sodium bicarbonate solution, and extracted with EtOAc (3×500 mL). The combined organic extracts were dried over $Na_2SO_4$, filtered, and concentrated under reduced pressure to give a white solid residue which was subjected to column chromatography using $CH_2Cl_2/MeOH/NH_4OH$ (200:10:1) as the eluent to give pure 6-hydroxy-buspirone (I, 7.2 g) and a mixture of buspirone and 6-hydroxy-buspirone (I). The mixture was purified by above column chromatography to afford another 3.3 g of pure 6-hydroxy-buspirone (I).

$^1H$ NMR ($CDCl_3$) δ 8.30 (d, J=4.7 Hz, 2H), 6.48 (t, J=4.7 Hz, 1H), 4.20 (s, 1H), 3.83–3.72 (m, 5H), 3.55 (s, 1H), 2.80 (d, J=17.5 Hz, 1H), 2.55–2.40 (m, 7H), 2.09–2.03 (m, 1H), 1.76–1.54 (m, 10H), 1.41–1.36 (m, 1H) 1.23–1.20 (m, 1H).

EXAMPLE 4

5-HT1A Receptor Binding Assay

Membranes are prepared for binding using the human 5-HT1A receptor expressed in HEK293 cells. Cells are collected and ruptured using a dounce homogenizer. The cells are spun at 18000×g for 10 minutes and the pellet is resuspended in assay buffer, frozen in liquid nitrogen and kept at −80° C. until the day of the assay.

A total of 30 ug protein is used per well. The assay is carried out in 96-deep-well plates. The assay buffer is 50 mM HEPES containing 2.5 mM $MgCl_2$ and 2 mM EGTA. The membrane preparation is incubated at 25° C. for 60 minutes with 0.1 nM to 1000 nM test compound and 1 nM 3H-8-OH-DPAT. 10 mM serotonin serves as blocking agent to determine non-specific binding. The reaction is terminated by the addition of 1 ml of ice cold 50 mM HEPES buffer and rapid filtration through a Brandel Cell Harvester using Whatman GF/B filters. The filter pads are counted in an LKB Trilux liquid scintillation counter. $IC_{50}$ values are determined using non-linear regression by Excel-fit.

EXAMPLE 5

Rat Pup Isolation-Induced Ultrasonic Vocalization Test

Harlan Sprague-Dawley rat pups (male and female) were housed in polycarbonate cages with the dam until 9–11 days old. Thirty minutes before testing, pups were removed from the dam, placed into a new cage with a small amount of home bedding and brought into the lab and placed under a light to maintain body temperature at 37° C. Pups were then weighed, sexed, marked and returned to the litter group until behavioral assessment. Testing took place in a Plexiglas recording chamber that contained a metal plate maintained at (18–20° C.) with a 5×5 cm grid drawn on the plate. A microphone was suspended 10 cm above the plate to record ultrasonic vocalizations. Ultrasonic calls were recorded using the Noldus UltraVox system providing online analysis of the frequency and duration of calls. The number of grid cells entered by the pup was also collected by visual scoring. Pups that failed to emit at least 60 calls during a 5 minute pretest session were excluded from pharmacological assessment. Immediately following the collection of the baseline measures, pups were injected with vehicle or drug subcutaneously at the nape of the neck and returned to its littermates. Thirty minutes later, pups were retested on each of the dependent measures (vocalization and grid cell crossings) to assess drug effects. Unless otherwise specified, each pup was used only once. Baseline differences and percent change from baseline for the frequency of ultrasonic vocalizations and grid cell crossings were analyzed using a one-way ANOVA. Bonferroni/Dunn post hoc comparisons were performed to assess the acute drug effects with vehicle control. Log-probit analysis was used to estimate the dose (milligrams per kilogram) of each agonist predicted to inhibit isolation-induced ultrasonic vocalizations by 50% ($ID_{50}$). All comparison were made with an experimental type I error rate (α) set at 0.05.

Doses for each drug were administered in an irregular order across several litters. S-6-hydroxy-buspirone and racemic 6-hydroxy-buspirone were dissolved in physiological saline (0.9% NaCl; vehicle). All injections were administered subcutaneously in a volume of 10 ml/kg. Doses of the drug refer to weight of the salt.

What is claimed is:

1. S-6-hydroxy-buspirone, substantially free of its R-stereoisomer, or a pharmaceutically acceptable salt or hydrate thereof.

2. A method for ameliorating a clinical disorder selected from the following: anxiety, depression and anxiety mixed with depression the method comprising the systemic administration of an effective but non-toxic dose of S-6-hydroxy-buspirone or a pharmaceutically acceptable salt or hydrate thereof.

3. The method of claim 2 wherein the route of administration of S-hydroxy-buspirone is selected from buccal, sublingual, transdermal, transnasal and oral.

4. The method of claim 3 wherein S-hydroxy-buspirone is administered orally.

5. A pharmaceutical composition comprising S-6-hydroxy-buspirone, substantially free of its R-stereoisomer and a pharmaceutically acceptable carrier.

6. A pharmaceutical composition according to claim 5, in the form of a tablet or capsule.

7. A method of preparing S-6-hydroxy-buspirone comprising the consecutive steps of:

a) treating buspirone with $KN(SiMe_3)_2$ prior to reacting with 2-(phenylsulfonyl)-3-phenloxaziridine to provide racemic 6-hydroxy-buspirone (I); and b) separating the enantiomers by means of chiral HPLC chromatography to afford S-6-hydroxy-buspirone (II).

* * * * *